(12) United States Patent
Noji (10) Patent No.: US 10,891,732 B2
(45) Date of Patent: Jan. 12, 2021

(54) DYNAMIC IMAGE PROCESSING SYSTEM

(71) Applicant: KONICA MINOLTA, INC., Tokyo (JP)

(72) Inventor: Sho Noji, Kokubunji (JP)

(73) Assignee: KONICA MINOLTA, INC., Tokyo (JP)

( * ) Notice: Subject to any disclaimer, the term of this patent is extended or adjusted under 35 U.S.C. 154(b) by 308 days.

(21) Appl. No.: 15/863,149

(22) Filed: Jan. 5, 2018

(65) Prior Publication Data
US 2018/0204326 A1 Jul. 19, 2018

(30) Foreign Application Priority Data

Jan. 13, 2017 (JP) .................. 2017-004009

(51) Int. Cl.
*G06K 9/46* (2006.01)
*G06T 7/00* (2017.01)
*A61B 6/00* (2006.01)
*G06T 7/11* (2017.01)
*G06T 7/174* (2017.01)
(Continued)

(52) U.S. Cl.
CPC ............ *G06T 7/0014* (2013.01); *A61B 6/469* (2013.01); *A61B 6/503* (2013.01); *A61B 6/504* (2013.01); *A61B 6/5217* (2013.01); *G06K 9/0053* (2013.01); *G06K 9/4609* (2013.01); *G06K 9/6202* (2013.01); *G06T 7/0016* (2013.01); *G06T 7/11* (2017.01); *G06T 7/174* (2017.01); *G06T 7/248* (2017.01); *G06K 2209/051* (2013.01); *G06T 2207/10016* (2013.01); *G06T 2207/10116* (2013.01); *G06T 2207/20104* (2013.01); *G06T 2207/30048* (2013.01); *G06T 2207/30104* (2013.01)

(58) Field of Classification Search
CPC .......... G06T 7/337; G06T 7/30; G06T 7/248; G06T 7/0012; G06T 7/0014; G06T 7/20; G06T 2207/10116; G06T 2207/10124; G06T 7/0028; G06T 7/11; G06T 7/174; G06T 7/0016; G06K 9/20; G06K 9/00208; G06K 9/4642; G06K 9/0053; G06K 9/4609; G06K 9/6202; A61B 6/5235; A61B 6/5229; A61B 6/5247; A61B 6/5258; A61B 6/585; A61B 6/032; A61B 6/4258; A61B 6/5223; A61B 6/5264; A61B 6/469; A61B 6/503; A61B 6/504; A61B 6/5217; A61N 5/1048; A61N 5/1049
See application file for complete search history.

(56) References Cited

U.S. PATENT DOCUMENTS 9,198,628 B2* 12/2015 Shimada .............. A61B 6/4291
2012/0300904 A1* 11/2012 Shimada .............. A61B 6/4291
378/62

FOREIGN PATENT DOCUMENTS

JP 2014135990 A 7/2014

* cited by examiner

*Primary Examiner* — Duy M Dang
(74) *Attorney, Agent, or Firm* — Lucas & Mercanti, LLP (57) ABSTRACT

A dynamic image processing system including a hardware processor that extracts a heart region from a chest dynamic image which is obtained by radiation imaging of a dynamic state at a chest, extracts a density waveform for each pixel in the extracted heart region, determines an extraction target candidate region of blood flow information based on the extracted density waveform for each pixel, and sets an extraction target region of the blood flow information in the determined extraction target candidate region of the blood flow information.

15 Claims, 6 Drawing Sheets

(51) Int. Cl.
*G06T 7/246* (2017.01)
*G06K 9/62* (2006.01)
*G06K 9/00* (2006.01)

DYNAMIC IMAGE PROCESSING SYSTEM

BACKGROUND

1. Technological Field

The present invention relates to a dynamic image processing system.

2. Description of the Related Art

In recent years, proposals have been made to extract a heart region from a chest dynamic image and present a density waveform of the extracted heart region as blood flow information or use the density waveform for analysis, the chest dynamic image being obtained by emitting X-rays to a chest of a human body and performing dynamic imaging.

As a technique for extracting the heart region, for example, Patent Document 1 (Japanese Patent Application Laid-Open Publication No. 2014-135990) describes extracting a left ventricle region from three-dimensional medical image data and extracting at least one region from among a right ventricle region, a left atrium region and a right atrium region on the basis of positional information of the extracted left ventricle region.

However, the chest dynamic image is a two-dimensional image, and even in the heart region, there are regions where the density waveform is not stable and disturbed by location as in the following regions, for example:

region where another heart region (for example, left atrium region) overlaps the back side of the heart region (for example, left ventricle region);

region where another structure such as a lumbar spine and a diaphragm overlaps the heart region; and region which is hypertrophied due to cardiac hypertrophy and such like (muscle region)

Thus, there has been a problem that when a density waveform is extracted from such a region, the density waveform is disturbed and correct blood flow information cannot be obtained.

SUMMARY

An object of the present invention is to acquire blood flow information of a stable density waveform from a heart region in a chest dynamic image.

To achieve at least one of the abovementioned objects, according to an aspect of the present invention, a dynamic image processing system reflecting one aspect of the present invention includes a hardware processor that extracts a heart region from a chest dynamic image which is obtained by radiation imaging of a dynamic state at a chest, extracts a density waveform for each pixel in the extracted heart region, determines an extraction target candidate region of blood flow information based on the extracted density waveform for each pixel, and sets an extraction target region of the blood flow information in the determined extraction target candidate region of the blood flow information.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

Hereinafter, one or more embodiments of the present invention will be described with reference to the drawings. However, the scope of the invention is not limited to the disclosed embodiments or illustrated examples.

[Configuration of Dynamic image processing system 100]

First, the configuration in an embodiment will be described.

Figure 1:
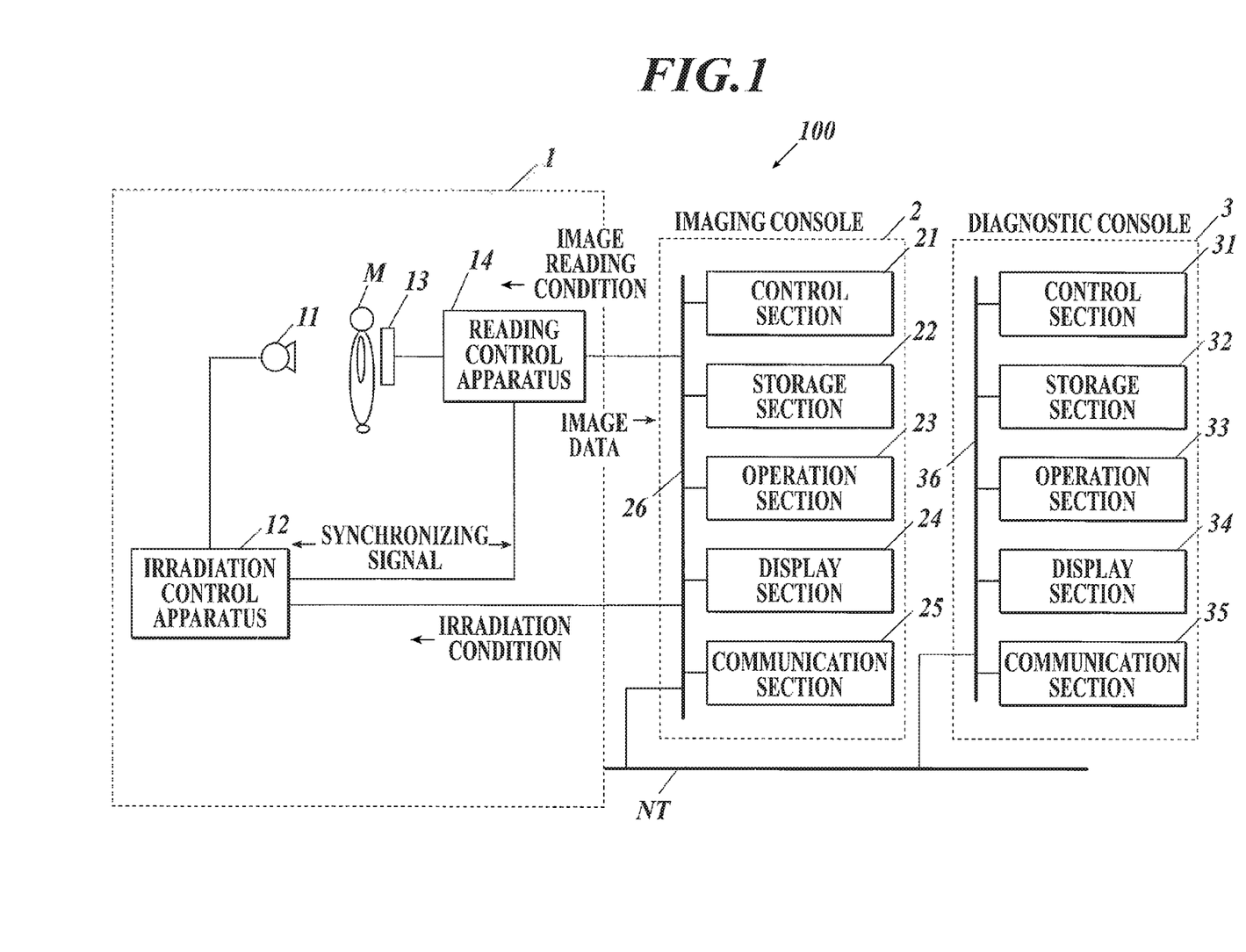
FIG. 1 is a view showing the entire configuration of a dynamic image processing system in an embodiment of the present invention.

FIG. 1 shows the entire configuration of a dynamic image processing system 100 in the embodiment.

As shown in FIG. 1, the dynamic image processing system 100 is configured by connecting an imaging apparatus 1 to an imaging console 2 via a communication cable or the like, and connecting the imaging console 2 to a diagnostic console 3 via a communication network NT such as a LAN (Local Area Network). The apparatuses forming the dynamic image processing system 100 are compliant with the DICOM (Digital Image and Communications in Medicine) standard, and the apparatuses are communicated with each other according to the DICOM.

[Configuration of Imaging Apparatus 1]

The imaging apparatus 1 performs imaging of a dynamic state which has periodicity (cycle), such as the state change of inflation and deflation of a lung according to the respiration movement and the heartbeat, for example. The dynamic imaging means obtaining a plurality of images showing a dynamic state by repeatedly emitting a pulsed radiation such as X-rays to a subject at a predetermined time interval (pulse irradiation) or continuously emitting the radiation (continuous irradiation) at a low dose rate without interruption. A series of images obtained by the dynamic imaging is referred to as a dynamic image.

Each of the plurality of images forming the dynamic image is referred to as a frame image. Hereinafter, the embodiment will be described by taking, as an example, a case where dynamic imaging of a chest is performed by the pulse irradiation A radiation source 11 is located at a position facing a radiation detection section 13 through a subject M (patient being tested), and emits radiation (X-rays) to the subject M in accordance with control of an irradiation control apparatus 12.

The irradiation control apparatus 12 is connected to the imaging console 2, and performs radiation imaging by controlling the radiation source 11 on the basis of an irradiation condition which was input from the imaging console 2. The irradiation condition input from the imaging console 2 is a pulse rate, a pulse width, a pulse interval, the number of imaging frames per imaging, a value of X-ray tube current, a value of X-ray tube voltage and a type of applied filter, for example. The pulse rate is the number of irradiation per second and consistent with an after-mentioned frame rate. The pulse width is an irradiation time required for one irradiation. The pulse interval is a time from start of one irradiation to start of the next irradiation, and consistent with an after-mentioned frame interval.

The radiation detection section 13 is configured by including a semiconductor image sensor such as an FPD. The FPD has a glass substrate, for example, and a plurality of detection elements (pixels) is arranged in matrix at a predetermined position on the substrate to detect, according to the intensity, radiation which was emitted from the radiation source 11 and has transmitted through at least the subject M, and convert the detected radiation into electric signals to be accumulated. Each pixel is formed of a switching section such as a TFT (Thin Film Transistor), for example. The FPD may be an indirect conversion type which converts an X-ray into an electrical signal by photoelectric conversion element via a scintillator, or may be a direct conversion type which directly converts an X-ray into an electrical signal.

The radiation detection section 13 is provided to face the radiation source 11 via the subject M.

The reading control apparatus 14 is connected to the imaging console 2. The reading control apparatus 14 controls the switching sections of respective pixels in the radiation detection section 13 on the basis of an image reading condition input from the imaging console 2, switches the reading of electric signals accumulated in the pixels, and reads out the electric signals accumulated in the radiation detection section 13 to obtain image data. The image data is a frame image. The reading control apparatus 14 outputs the obtained frame image to the imaging console 2. The image reading condition is, for example, a frame rate, frame interval, a pixel size and an image size (matrix size). The frame rate is the number of frame images obtained per second and consistent with the pulse rate. The frame interval is a time from start of obtaining one frame image to start of obtaining the next frame image, and consistent with the pulse interval.

Here, the irradiation control apparatus 12 and the reading control apparatus 14 are connected to each other, and transmit synchronizing signals to each other to synchronize the irradiation operation with the image reading operation.

[Configuration of Imaging console 2]

The imaging console 2 outputs the irradiation condition and the image reading condition to the imaging apparatus 1, controls the radiation imaging and the reading operation of radiation images by the imaging apparatus 1, and displays the dynamic image obtained by the imaging apparatus 1 so that an operator who performs the imaging such as an imaging operator confirms the positioning and whether the image is appropriate for diagnosis.

As shown in FIG. 1, the imaging console 2 is configured by including a control section 21, a storage section 22, an operation section 23, a display section 24 and a communication section 25, which are connected to each other via a bus 26.

The control section 21 is configured by including a CPU (Central Processing Unit), a RAM (Random Access Memory) and such like. According to the operation of the operation section 23, the CPU of the control section 21 reads out system programs and various processing programs stored in the storage section 22 to load the programs into the RAM, executes various types of processing including after-mentioned imaging control processing in accordance with the loaded programs, and integrally controls the operations of the sections in the imaging console 2 and the irradiation operation and the reading operation of the imaging apparatus 1.

The storage section 22 is configured by including a non-volatile semiconductor memory, a hard disk or the like. The storage section 22 stores various programs executed by the control section 21, parameters necessary for executing processing by the programs, and data of processing results. For example, the storage section 22 stores a program for executing the imaging control processing shown in FIG. 2. The storage section 22 stores the irradiation condition and the image reading condition so as to be associated with the examination target site (here, chest). The various programs are stored in a form of readable program code, and the control section 21 executes the operations according to the program code as needed.

The operation section 23 is configured by including a keyboard including cursor keys, numeric keys and various function keys and a pointing device such as a mouse. The operation section 23 outputs an instruction signal input by a key operation to the keyboard or a mouse operation to the control section 21. The operation section 23 may include a touch panel on the display screen of the display section 24. In this case, the operation section 23 outputs the instruction signal which is input via the touch panel to the control section 21.

The display section 24 is configured by a monitor such as an LCD (Liquid Crystal Display) and a CRT (Cathode Ray Tube), and displays instructions input from the operation section 23, data and such like in accordance with an instruction of a display signal input from the control section 21.

The communication section 25 includes a LAN adapter, a modem, a TA (Terminal Adapter) and such like, and controls the data transmission and reception with the apparatuses connected to the communication network NT.

[Configuration of Diagnostic Console 3]

The diagnostic console 3 is an apparatus for obtaining the dynamic image from the imaging console 2 and displaying the obtained dynamic image and an analysis result of the dynamic image to support diagnosis by a doctor.

As shown in FIG. 1, the diagnostic console 3 is configured by including a control section 31, a storage section 32, an operation section 33, a display section 34 and a communication section 35, which are connected to each other via a bus 36.

The control section 31 is configured by including a CPU, a RAM and such like. According to the operation of the operation section 33, the CPU of the control section 31 reads out system programs stored in the storage section 32 and various processing programs to load them into the RAM, executes the various types of processing including after-mentioned blood flow information extraction processing in accordance with the loaded program, and integrally controls the operation of the sections in the diagnostic console 3.

The storage section 32 is configured by including a nonvolatile semiconductor memory, a hard disk or the like. The storage section 32 stores various programs including a program for executing the blood flow information extraction processing by the control section 31, parameters necessary for executing processing by the programs and data of processing results or the like. The various programs are stored in a form of readable program code, and the control section 31 executes the operations according to the program code as needed.

The operation section 33 is configured by including a keyboard including cursor keys, numeric keys and various function keys and a pointing device such as a mouse, and outputs an instruction signal input by a key operation to the keyboard and a mouse operation by a user to the control section 31. The operation section 33 may include a touch panel on the display screen of the display section 34. In this case, the operation section 33 outputs an instruction signal, which was input via the touch panel, to the control section 31.

The display section 34 is configured by including a monitor such as an LCD and a CRT, and performs various displays in accordance with the instruction of a display signal input from the control section 31.

The communication section 35 includes a LAN adapter, a modem, a TA and such like, and controls data transmission and reception with the apparatuses connected to the communication network NT.

[Operation of Dynamic Image Processing System 100]

Next, the operation of the dynamic image processing system 100 in the embodiment will be described.

(Operations of Imaging Apparatus 1 and Imaging Console 2)

First, imaging operation by the imaging apparatus 1 and the imaging console 2 will be described.

Figure 2:
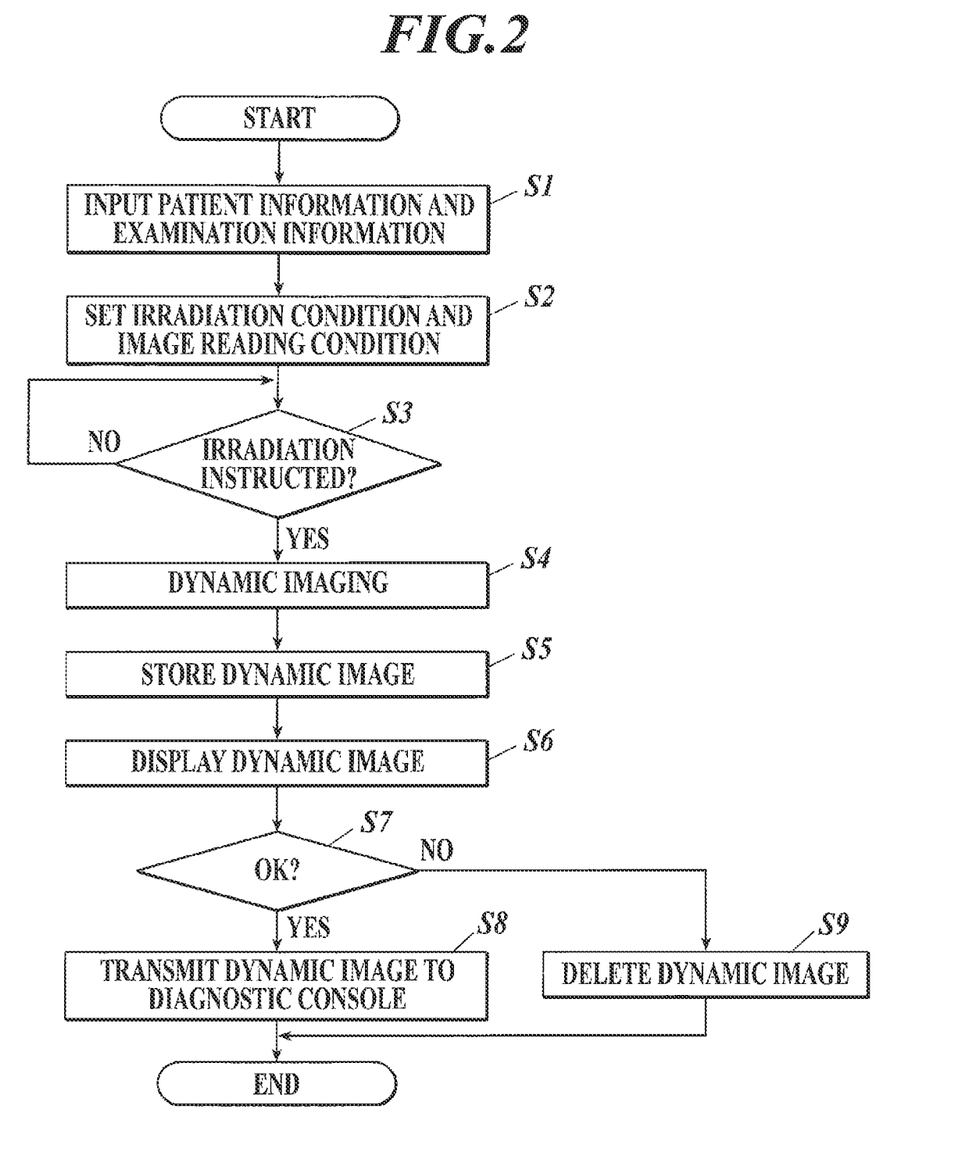
FIG. 2 is a flowchart showing imaging control processing which is executed by a control section of an imaging console in FIG. 1.

FIG. 2 shows imaging control processing executed by the control section 21 in the imaging console 2. The imaging control processing is executed in cooperation between the control section 21 and the program stored in the storage section 22.

First, the operator operates the operation section 23 in the imaging console 2, and inputs patient information (patient name, height, weight, age, sex and such like) of the patient being tested (subject M) and examination information (for example, examination target site (here, chest) and the type of the diagnosis target (for example, ventilation and blood flow) or the like) (step S1).

Next, the irradiation condition is read out from the storage section 22 and set in the irradiation control apparatus 12, and the image reading condition is read out from the storage section 22 and set in the reading control apparatus 14 (step S2).

An instruction of irradiation by the operation of the operation section 23 is waited (step S3). The operator locates the subject M between the radiation source 11 and the radiation detection section 13, and performs positioning. The operator instructs the patient being tested (subject M) regarding a breathing state. For example, the operator instructs the patient being tested (subject M) to be at ease to lead into quiet breathing. The operator may instruct the patient being tested (subject M) to perform quiet breathing in a case where the type of the diagnosis target is ventilation, and the operator may instruct the patient being tested (subject M) to hold the breath in a case where the type of the diagnosis target is blood flow. When the preparation for imaging is completed, the operator operates the operation section 23 to input the irradiation instruction.

When the irradiation instruction is input from the operation section 23 (step S3: YES), an imaging start instruction is output to the irradiation control apparatus 12 and the reading control apparatus 14, and the dynamic imaging is started (step S4). That is, radiation is emitted by the radiation source 11 at the pulse interval set in the irradiation control apparatus 12, and frame images are obtained by the radiation detection section 13.

When the imaging is finished for a predetermined number of frames, the control section 21 outputs an instruction to end the imaging to the irradiation control apparatus 12 and the reading control apparatus 14, and the imaging operation is stopped. The number of frames to be captured is a number which enables imaging of at least one respiratory cycle.

The frame images obtained by the imaging are input to the imaging console 2 in order, stored in the storage section 22 so as to be associated with respective numbers (frame numbers) indicating the imaging order (step S5), and displayed on the display section 24 (step S6). The operator confirms positioning and such like by the displayed dynamic image, and determines whether an image appropriate for diagnosis was acquired by the imaging (imaging was successful) or imaging needs to be performed again (imaging failed). The operator operates the operation section 23 and inputs the determination result.

If the determination result indicating that the imaging was successful is input by a predetermined operation of the operation section 23 (step S7: YES), each of a series of frame images obtained by the dynamic imaging is accompanied with information such as the identification ID for identifying the dynamic image, the patient information, the examination information, the irradiation condition, the image reading condition and the number (frame number) indicating the imaging order (for example, the information is written into a header region of the image data in the DICOM format), and transmitted to the diagnostic console 3 via the communication section 25 (step S8). Then, the processing ends. On the other hand, if the determination result indicating that the imaging failed is input by a predetermined operation of the operation section 23 (step S7: NO), the series of frame images stored in the storage section 22 is deleted (step S9), and the processing ends. In this case, the imaging needs to be performed again.

(Operation of Diagnostic Console 3)

Next, the operation of the diagnostic console 3 will be described.

Figure 3:
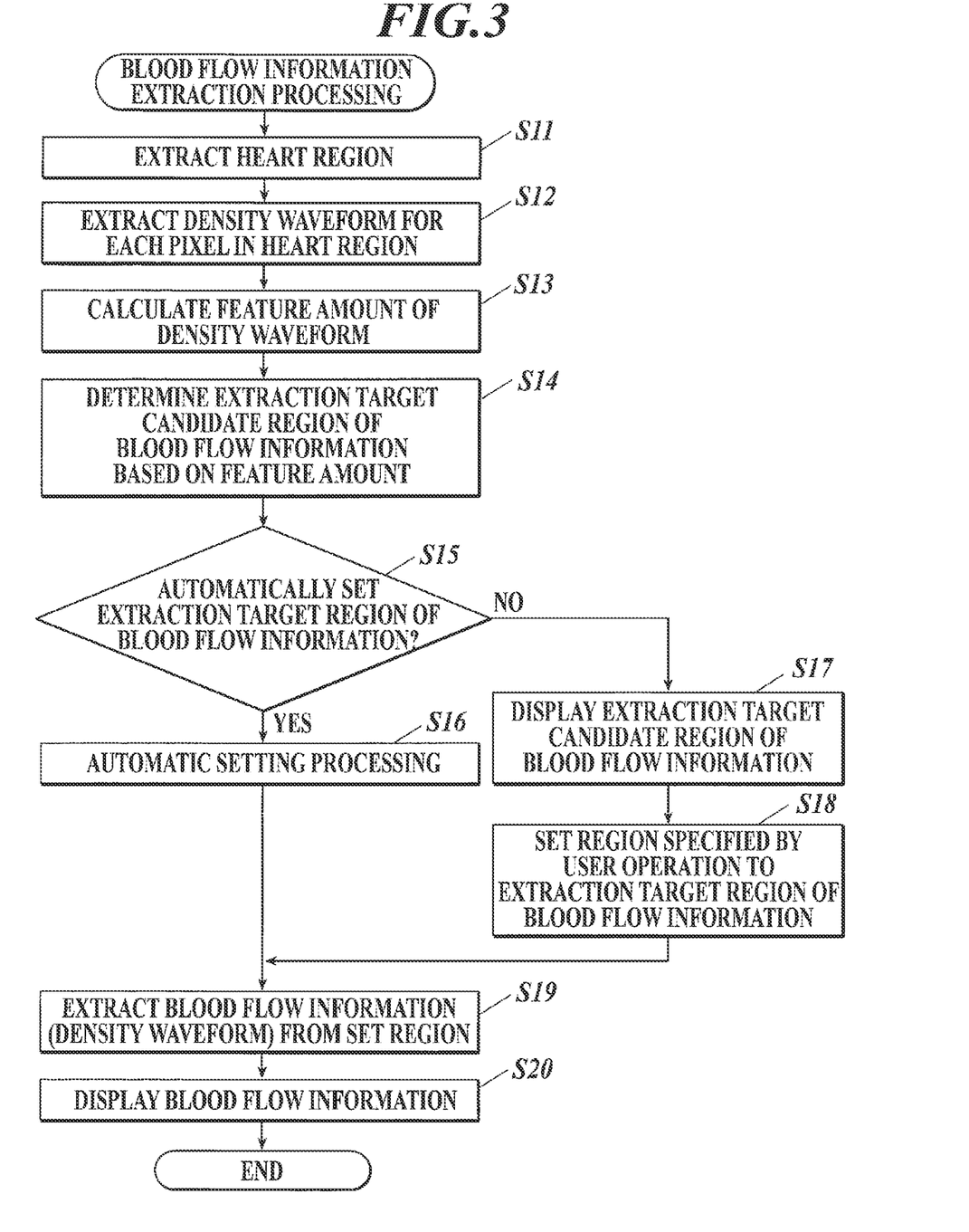
FIG. 3 is a flowchart showing blood flow information extraction processing which is executed by a control section of a diagnostic console in FIG. 1.

In the diagnostic console 3, when the series of frame images forming the dynamic image for which the type of the diagnosis target is blood flow is received from the imaging console 2 via the communication section 35, the blood flow information extraction processing shown in FIG. 3 is executed in cooperation between the control section 31 and the program stored in the storage section 32.

Hereinafter, the flow of the blood flow information extraction processing will be described with reference to FIG. 3.

First, a heart region is extracted from the received dynamic image (step S11).

The heart region can be extracted by using template matching, for example. For example, a template image of a heart is stored in the storage section 32, a degree of similarity between the template image and a portion overlapping the template image is calculated while moving the template image in one frame image of the dynamic image (for example, first frame image), and the region having the highest degree of similarity is extracted as the heart region. For the other frame images, the region of the same pixel positions (coordinates) as those of the heart region extracted from the one frame image is extracted as the heart region.

The degree of similarity can be calculated by using SSD (Sum of Squared Difference) shown in (formula 1), SAD (Sum of Absolute Difference) shown in (formula 2) and such like, for example. I (x, y) indicates a density value (pixel value) of a frame image, and T (x, y) indicates a density value of the template image. The degree of similarity is larger as the SSD and SAD have smaller values, and the values of the SSD and the SAD are 0 when the frame image completely matches the template image.

[Numerical formula 1]

$$SSD = \sum_{x=0}^{x-1} \sum_{y=0}^{y-1} (I(x, y) - T(x, y))^2 \quad \text{(formula 1)}$$

$$SAD = \sum_{x=0}^{x-1} \sum_{y=0}^{y-1} |I(x, y) - T(x, y)| \quad \text{(formula 2)}$$

The heart may be assumed to have a nearly spherical form, and the region satisfying the condition of the spherical form may be extracted as the heart region by using form recognition processing with Hessian matrix. For example, 2×2 Hessian matrix (formula 3) is calculated for each pixel in one frame image of the dynamic image, and eigenvalues λ1 and λ2 of the Hessian matrix are calculated. The two eigenvalues λ1 and λ2 of the two-dimensional Hessian matrix in the region of the spherical form have a property of satisfying the conditions that "the eigenvalues are sufficiently larger than 0" and "the magnitudes of the two eigenvalues are nearly same". Thus, whether the two eigenvalues λ1 and λ2 satisfy the conditions that "the eigenvalues are sufficiently larger than 0" and "the magnitudes of the two eigenvalues are nearly same" is determined, and the region of pixels which were determined to satisfy the conditions is extracted as the heart region. For the other frame images, the region of the same pixel positions (coordinates) as those of the heart region extracted from the one frame image is extracted as the heart region.

[Numerical formula 2]

$$H(x, \sigma) = \begin{bmatrix} L_{xx}(x, \sigma) & L_{xy}(x, \sigma) \\ L_{xy}(x, \sigma) & L_{yy}(x, \sigma) \end{bmatrix} \quad \text{(formula 3)}$$

$L_{ab}$ is a response value obtained by convolving the quadratic differential in each direction of Gaussian into image I(x)

$$L_{xx}(x, \sigma) = I(x) \otimes \frac{\partial^2}{\partial x^2} g(\sigma), \; L_{yy}(x, \sigma) = I(x) \otimes \frac{\partial^2}{\partial y^2} g(\sigma),$$

$$L_{xy}(x, \sigma) = I(x) \otimes \frac{\partial^2}{\partial x \partial y} g(\sigma)$$

The heart dilates/contracts by pulsation, and in accordance with this, the heart wall moves to the left and right. Thus, the heart region may be extracted by using movement information of the contour.

In the extraction processing of the heart region using the movement information of the contour, first, an edge (contour) is extracted from the first frame image of the dynamic image. For example, the edge is extracted by applying Laplacian filter to the first frame image. Next, the edge is searched for in a left and right direction from each pixel on a central line in a vertical direction of the first frame image, and ROIs are set on the detected edges. Next, by using each of the set ROIs as a template image, the degree of similarity (for example, SSD or SAD) between the template image and the portion overlapping the template image is calculated while moving the template image in each of the plurality of frame images following the first frame image. The region having the highest degree of similarity is extracted as the region of the ROI in the frame image. On the basis of the ROIs which were extracted from the plurality of frame images, the movement direction of the ROI is specified, and the region surrounded by ROIs having the movement direction which is a left and right direction is extracted as the heart region of the first frame image. For the other frame images, the region of the same pixel positions (coordinates) as those of the heart region extracted from the first frame image is extracted as the heart region.

In the above description, the movement direction is calculated by using the first frame image as a reference. However, the frame image as a reference may be changeable. For example, the frame image which is immediate before a frame image may be used as a reference by obtaining the ROI of the second frame image with template matching using the ROI of the first frame image as a template image, obtaining the ROI of the third frame image with the template matching using the ROI of the second frame image as the template image, and such like.

Next, the density waveform for each pixel in the heart region is extracted (step S12).

Figure 4:
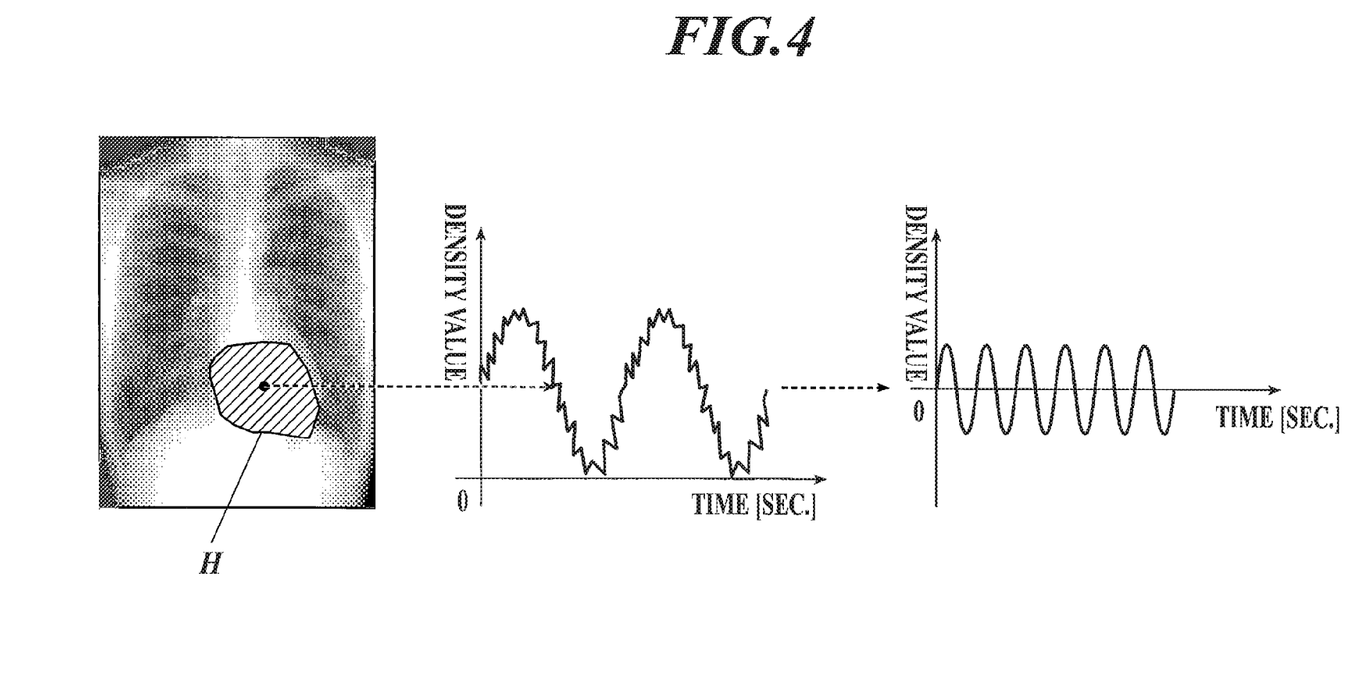
FIG. 4 is a view for explaining an extraction method of a density waveform.

In step S12, as shown in FIG. 4, the density waveform is extracted by plotting the density value of each pixel in the heart region H in time series (in the frame image order), and high-pass filtering (for example, cutoff frequency is 0.80 Hz) in the time direction is applied to the extracted density waveform. Thus, the low frequency component by the noise is removed from the density waveform and the density waveform by the blood flow can be extracted accurately. The low frequency component may be removed by using a band-pass filter (for example, cutoff frequency is 0.8 Hz in a low range and cutoff frequency is 2.4 Hz in a high range) to the density waveform.

Next, the feature amount of the extracted density waveform for each pixel is calculated (step S13).

In step S13, for example, a frequency component, an amplitude value or the like of the density waveform for each pixel are calculated.

Figure 5:
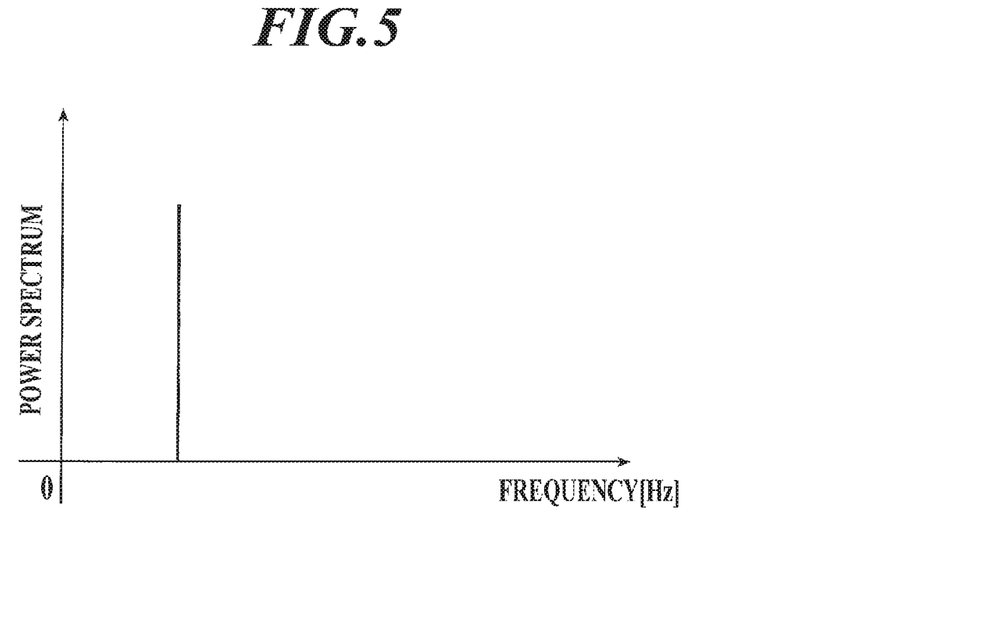
FIG. 5 is a view showing a frequency component of the density waveform which is calculated in step S13 of FIG. 3.
Figure 6:
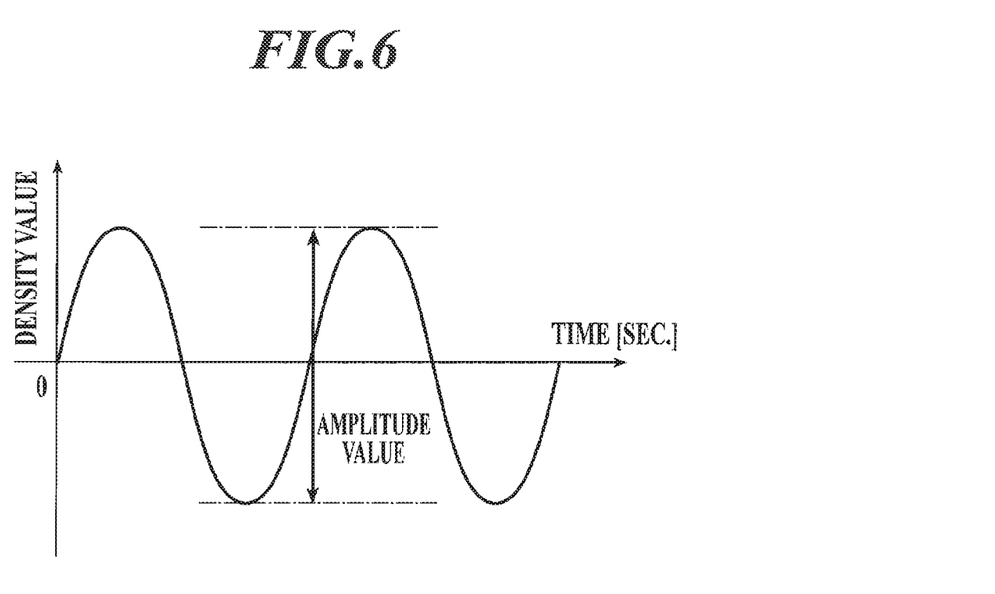
FIG. 6 is a view showing an amplitude value of the density waveform which is calculated in step S13 of FIG. 3.

The frequency component of the density waveform can be obtained by performing Fourier transform of the density waveform to calculate a power spectrum for each frequency, for example (see FIG. 5). The amplitude value can be obtained by subtracting a local minimum value from a local maximum value of the density waveform as shown in FIG. 6.

Next, on the basis of the calculated feature amount, the extraction target candidate region of the blood flow information is determined (step S14).

In step S14, for example, the extraction target candidate region of the blood flow information is determined by processing of any one of the following (1) to (3) or a combination thereof.

(1) First, for each pixel in the heart region, the number of peaks of the frequency components in the density waveform is measured. For example, for each pixel, the largest value of the calculated power spectrums is obtained, frequency components having power spectrums which are n % or more (n is a numerical value) of the largest value are determined to be peaks, and the number of peaks is counted. Or, the largest power spectrum among all the pixels in the heart region is obtained, and, for each pixel, frequency components having power spectrums of n % or more of the largest power spectrum are determined to be peaks, and the number of peaks is counted. Next, a threshold of the number of peaks is set on the basis of the number of peaks of the frequency components for all the pixels in the heart region. For example, an average number of peaks of the numbers of peaks for all the pixels is obtained, and the threshold of the number of peaks is set on the basis of the average number of peaks. The region of pixels having the numbers of peaks which are equal to or lower than the set threshold is determined to be the extraction target candidate region of the blood flow information. The threshold may be preset by the operation section 33 in advance. The above n can be set by the operation section 33.

It can be said that the density waveform is less disturbed and more stable as the number of peaks of the frequency components is smaller. It can be said that, as the number of peaks is larger, more frequency components are mixed and the density waveform is more disturbed. Thus, by determining the region having the number of peaks of the density waveform which is equal to or smaller than the threshold in the heart region to be the extraction target candidate region of the blood flow information, it is possible to determine the region providing a density waveform which is stable and not disturbed to be an extraction target of the blood flow information. The desirable threshold of the number of peaks is 1.

(2) The dynamic image processing system 100 is configured to include an electrocardiograph as a heart rate acquisition section, the heart rate (bpm) of the subject M is acquired in synchronization with the dynamic imaging, and the acquired heart rate is divided by 60 to be converted into the frequency (Hz). The region of pixels where a peak exists at the frequency of density waveform nearly matching the converted frequency is determined to be the extraction target candidate region of the blood flow information.

In such a way, by determining the region where the peak of the frequency of the density waveform exists at the frequency of the heartbeat to be the extraction target candidate region of the blood flow information, the region providing the density waveform corresponding to the heartbeat can be determined as the extraction target of the blood flow information.

(3) The largest amplitude value is obtained from among all the pixels in the heart region, and the region of the pixels having the amplitude values which are m % or more (m is a numerical value) of the largest amplitude value is determined to be the extraction target candidate region of the blood flow information. Or, the average value of the amplitude values of all the pixels in the heart region is obtained, and the region of the pixels having the amplitude values which are the average value or more, or m % or more of the average value is determined to be the extraction target candidate region of the blood flow information.

In this way, by excluding the regions in the heart region having small amplitude of the density waveform from the extraction target of the blood flow information, the noise component can be removed from the extraction target of the blood flow information.

Next, whether to automatically set the extraction target region of the blood flow information is determined (step S15). Whether or not to automatically set the extraction target region can be preset by the operation section 33.

If it is determined to automatically set the extraction target region of the blood flow information (step S15; YES), automatic setting processing is executed (step S16), and the processing proceeds to step S19.

Figure 7A:
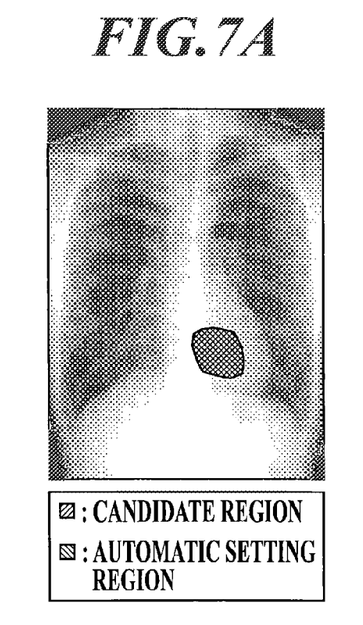
FIG. 7A is a view showing an example of setting an extraction target candidate region of the blood flow information determined in step S14 as an extraction target region of the blood flow information in step S16 of FIG. 3.
Figure 7B:
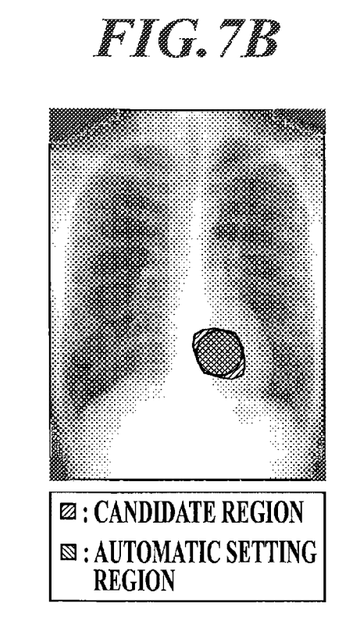
FIG. 7B is a view showing an example of setting a circle having a largest area which is included in the extraction target candidate region of the blood flow information determined in step S14 as an extraction target region of the blood flow information in step S16 of FIG. 3.
Figure 7C:
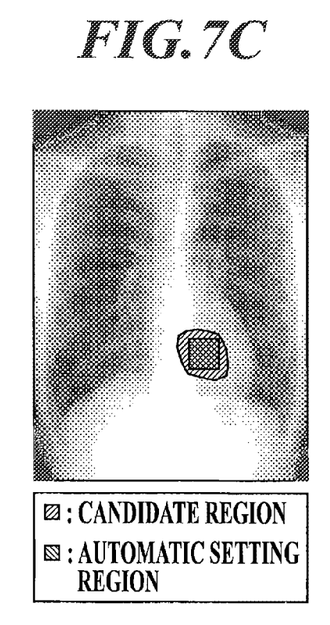
FIG. 7C is a view showing an example of setting a polygonal region having a largest area which is included in the extraction target candidate region of the blood flow information determined in step S14 as an extraction target region of the blood flow information in step S16 of FIG. 3.

In step S16, for example, as shown in FIG. 7A, the extraction target candidate region of the blood flow information which was determined in step S14 is set as the extraction target region of the blood flow information. Or, as shown in FIGS. 7B and 7C, the region which is a circle (including an ellipse) or a polygon having the largest area and included in the extraction target candidate region of the blood flow information that was determined in step S14 is set as the extraction target region of the blood flow information. Or, the centroid of the extraction target candidate region of the blood flow information which was determined in step S14 is calculated, and on the basis of the position of the centroid as a reference (for example, as a center), the region having a size and a shape which were set in advance is set as the extraction target region of the blood flow information.

Figure 7D:
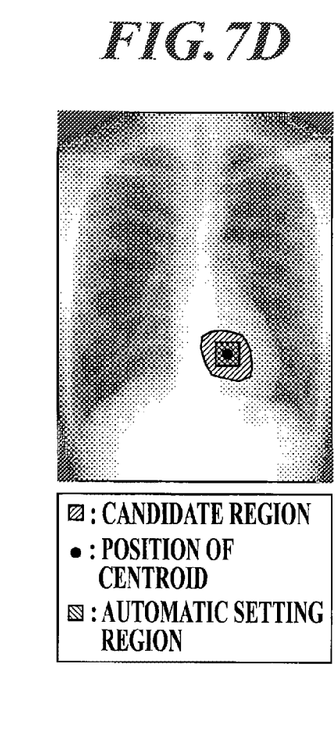
FIG. 7D is a view showing an example of setting a region as an extraction target region of the blood flow information in step S16 of FIG. 3, the region having a predetermined size and a predetermined shape based on, as a reference, the position of the centroid of the extraction target candidate region of the blood flow information which was determined in step S14.

As shown in FIGS. 7A to 7C, by setting as large an extraction target region of the blood flow information as possible in the extraction target candidate region of the blood flow information, it is possible to extract the blood flow information stably by suppressing the influence of noise. As shown in FIG. 7D, by setting the extraction target region of the blood flow information in an arbitrary size, it is possible to make the size of the extraction target region of the blood flow information be the same size as the size which was set for a lung field in a case where the blood flow information is to be compared with the lung field, for example. At this time, by setting the extraction target region to a specific position (for example, centroid) of the extraction target candidate region of the blood flow information, it is possible to suppress the influence of noise.

If it is not determined to automatically set the extraction target region of the blood flow information (if it is determined to manually set the extraction target region) (step S15; NO), the extraction target candidate region of the blood flow information (dynamic image including the extraction target region) is displayed on the display section 34 (step S17). The region which was specified by the operation section 33 in the extraction target candidate region of the blood flow information is set as the extraction target region of the blood flow information (step S18), and the processing proceeds to step S19.

In step S19, the density waveform is extracted as the blood flow information from the extraction target region of the blood flow information which was set in the dynamic image (step S19). In detail, first, a representative value of density values (for example, average value, median value, maximum value or the like) is calculated for the extraction target region of the blood flow information of each frame image in the dynamic image, the density waveform is extracted by plotting the calculated representative value in time series (in the frame image order), and high-pass filtering (for example, cutoff frequency is 0.80 Hz) in the time direction is applied to the extracted density waveform. The low frequency component may be removed by using a band-pass filter (for example, cutoff frequency is 0.8 Hz in a low range and cutoff frequency is 2.4 Hz in a high range) to the density waveform.

The extracted blood flow information is displayed on the display section 34 (step S20), and the blood flow information extraction processing ends.

In this way, in the dynamic image processing system 100, the extraction target candidate region of the blood flow information is determined in the heart region, which was extracted from the dynamic image, on the basis of the feature amount of the density waveform, the density waveform is extracted from the extraction target region which was set in the determined extraction target candidate region, and the extracted density waveform is displayed as blood flow information. Accordingly, since blood flow information of a stable density waveform can be acquired from the heart region of the chest dynamic image and displayed, the heart region can be diagnosed stably.

Though the density waveform extracted in step S19 is displayed on the display section 34 in the blood flow information extraction processing shown in FIG. 3, the density waveform may be used for analysis of the dynamic image.

For example, as described in Japanese Patent Application Laid-Open Publication No. 2012-5729, the density waveform which was extracted in step S19 can be used as the pulse signal waveform in analysis processing in which, while the blood flow signal waveform (density waveform) for each pixel or each sub-region of the lung field region of the dynamic image is shifted by one frame interval (shifted in the time direction) with respect to a pulse signal waveform, the cross-correlation coefficient between the pulse signal waveform and the blood flow signal waveform is calculated to generate an image in which the color corresponding to the maximum cross-correlation coefficient among a plurality of cross-correlation coefficients is added to each pixel or each sub-region, the plurality of cross-correlation coefficients being calculated by the above shift for a total of one heartbeat period or more. Thus, since it is possible to perform analysis on the basis of the stable pulse signal waveform as a reference, stable analysis processing can be made.

As described above, according to the diagnostic console 3 in the dynamic image processing system 100, the control section 31 extracts a heart region from a chest dynamic image, extracts a density waveform for each pixel in the extracted heart region, and calculates a feature amount of the density waveform for each pixel. The control section 31 determines an extraction target candidate region of the blood flow information on the basis of the calculated feature amount of the density waveform for each pixel, and sets an extraction target region of the blood flow information in the determined extraction target candidate region of the blood flow information.

Accordingly, since it is possible to acquire the blood flow information of the stable density waveform from the heart region of the chest dynamic image and display the acquired blood flow information, the heart region can be diagnosed and analyzed stably.

For example, the control section 31 applies filtering in the time direction to the density waveform for each pixel in the heart region and removes the low frequency component. Thus, it is possible to accurately extract the density waveform of the blood flow component.

For example, the control section 31 calculates the frequency component of the density waveform as the feature amount of the density waveform, measures the number of peaks of the frequency components of the density waveform for each pixel, and determines the region of the pixels having the number of peaks which is equal to or smaller than a predetermined threshold to the extraction target candidate region of the blood flow information. Thus, it is possible to determine the region providing the density waveform which is stable and not disturbed to be the extraction target of the blood flow information.

For example, the control section 31 converts the heart rate of the subject which was acquired during imaging of the chest dynamic image into the frequency, and determines the region of pixels having a peak at the frequency of density waveform which nearly matches the converted frequency to be the extraction target candidate region of the blood flow information. Thus, it is possible to determine the region providing the density waveform corresponding to the heart beat to be the extraction target of the blood flow information.

For example, the control section 31 calculates an amplitude value as the feature amount of the density waveform, calculates a threshold of the amplitude value on the basis of the amplitude values of all the pixels in the heart region and determines the region of pixels having the amplitude values which are larger than the threshold to be the extraction target candidate region of the blood flow information. Thus, it is possible to remove the noise component from the extraction target of the blood flow information.

For example, the control section 31 sets the region which was specified by user's operation on the extraction target candidate region of the blood flow information displayed on the display section 34 to be the extraction target region of the blood flow information. Thus, it is possible to set, as the extraction target region of the blood flow information, the region which is desired by the user in the extraction target candidate region.

For example, the control section 31 automatically sets, as the extraction target region of the blood flow information, the entire extraction target candidate region of the blood flow information, the region which is a circle or a polygon having the largest area and included in the extraction target candidate region of the blood flow information, or the region having an arbitrary shape and an arbitrary size based on the position of the centroid as a reference in the extraction target candidate region of the blood flow information. Accordingly, it is possible to automatically set the extraction target region of the blood flow information from the extraction target candidate region.

Though the embodiments of the present invention have been described above, the description in the embodiments is a preferred example of the present invention, and the present invention is not limited to the above description.

For example, the above description discloses an example of using a hard disk, a semiconductor non-volatile memory or the like as a computer readable medium of the program according to the present invention. However, the present invention is not limited to this example. A portable recording medium such as a CD-ROM can be applied as a computer readable medium. A carrier wave is also applied as the medium for providing program data according to the present invention via a communication line.

As for the other detailed configurations and detailed operations of the apparatuses forming the dynamic image processing system, modifications can be appropriately made within the scope of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2017-004009 filed on Jan. 13, 2017 is incorporated herein by reference in its entirety.

What is claimed is:

1. A dynamic image processing system comprising a hardware processor that extracts a heart region from a chest dynamic image which is obtained by radiation imaging of a dynamic state at a chest, extracts a density waveform for each pixel in the extracted heart region, determines an extraction target candidate region of blood flow information based on the extracted density waveform for each pixel, and sets an extraction target region of the blood flow information in the determined extraction target candidate region of the blood flow information, wherein the hardware processor calculates a feature amount of the extracted density waveform for each pixel, and determines the extraction target candidate region of the blood flow information based on the calculated feature amount for each pixel.

2. The dynamic image processing system according to claim 1, wherein the hardware processor extracts the heart region from one frame image in the chest dynamic image by using template matching, and extracts the heart region from each frame image in the chest dynamic image based on the heart region extracted from the one frame image.

3. The dynamic image processing system according to claim 1, wherein the hardware processor calculates a Hessian matrix for each pixel in one frame image in the chest dynamic image, calculates an eigenvalue from the Hessian matrix, extracts the heart region from the one frame image based on the eigenvalue, and extracts the heart region from each frame image in the chest dynamic image based on the heart region extracted from the one frame image.

4. The dynamic image processing system according to claim 1, wherein the hardware processor extracts a contour from a plurality of frame images in the chest dynamic image, and extracts a heart region from each frame image in the chest dynamic image based on a movement direction of the extracted contour.

5. The dynamic image processing system according to claim 1, wherein the hardware processor applies filtering in a time direction to the extracted density waveform to remove a low frequency component.

6. The dynamic image processing system according to claim 1, wherein the hardware processor calculates a frequency component of the density waveform as the feature amount.

7. The dynamic image processing system according to claim 6, wherein the hardware processor measures a number of a peak of the calculated frequency component of the density waveform for each pixel, and determines a region of a pixel having the number of peaks which is equal to or smaller than a predetermined threshold to be the extraction target candidate region of the blood flow information.

8. The dynamic image processing system according to claim 6, wherein the hardware processor acquires a heart rate of a subject during imaging of the chest dynamic image, converts the acquired heart rate into a frequency, and determines a region of a pixel which has a peak at a frequency of the density waveform nearly matching the converted frequency to be the extraction target candidate region of the blood flow information.

9. The dynamic image processing system according to claim 1, wherein the hardware processor calculates an amplitude value of the density waveform as the feature amount.

10. The dynamic image processing system according to claim 9, wherein the hardware processor calculates a threshold of the amplitude value, and determines a region of a pixel having the calculated amplitude value which is larger than the threshold to be the extraction target candidate region of the blood flow information.

11. The dynamic image processing system according to claim 10, wherein the hardware processor calculates the threshold of the amplitude value based on amplitude values of all pixels in the heart region.

12. The dynamic image processing system according to claim 1, further comprising a display which displays the extraction target candidate region of the blood flow information, wherein the hardware processor sets, as the extraction target region of the blood flow information, a region which is specified by user's operation on the extraction target candidate region of the blood flow information that is displayed on the display.

13. The dynamic image processing system according to claim 1, wherein the hardware processor sets an entire extraction target candidate region of the blood flow information as the extraction target region of the blood flow information.

14. The dynamic image processing system according to claim 1, wherein the hardware processor sets, as the extraction target region of the blood flow information, a region which is a circle or a polygon having a largest area and included in the extraction target candidate region of the blood flow information.

15. The dynamic image processing system according to claim 1, wherein the hardware processor calculates a position of a centroid of the extraction target candidate region of the blood flow information, and sets, as the extraction target region of the blood flow information, a region which has an arbitrary shape and an arbitrary size based on the position of the centroid as a reference in the extraction target candidate region of the blood flow information.

* * * * *